United States Patent
Kim et al.

(10) Patent No.: US 10,143,433 B2
(45) Date of Patent: Dec. 4, 2018

(54) COMPUTED TOMOGRAPHY APPARATUS AND METHOD OF RECONSTRUCTING A COMPUTED TOMOGRAPHY IMAGE BY THE COMPUTED TOMOGRAPHY APPARATUS

(71) Applicant: SAMSUNG ELECTRONICS CO., LTD., Suwon-si (KR)

(72) Inventors: Gye-hyun Kim, Seoul (KR); Jae-sung Lee, Seoul (KR); Jae-chool Lee, Suwon-si (KR); Hae-kyung Jung, Seongnam-si (KR); Yoon-mi Hong, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/118,691

(22) PCT Filed: Feb. 12, 2015

(86) PCT No.: PCT/KR2015/001412
§ 371 (c)(1),
(2) Date: Aug. 12, 2016

(87) PCT Pub. No.: WO2015/122698
PCT Pub. Date: Aug. 20, 2015

(65) Prior Publication Data
US 2017/0042494 A1  Feb. 16, 2017

(30) Foreign Application Priority Data
Feb. 12, 2014 (KR) .................. 10-2014-0016275

(51) Int. Cl.
*A61B 6/00* (2006.01)
*A61B 6/03* (2006.01)
(Continued)

(52) U.S. Cl.
CPC ............ *A61B 6/5205* (2013.01); *A61B 6/032* (2013.01); *A61B 6/461* (2013.01); *A61B 6/5258* (2013.01);
(Continued)

(58) Field of Classification Search
CPC ......... A61B 6/025; A61B 6/032; A61B 6/502; A61B 6/5205; A61B 6/5258; A61B 6/563;
(Continued)

(56) References Cited

U.S. PATENT DOCUMENTS 6,263,096 B1 *  7/2001  Boag ..................... G06T 11/001
                                                   378/65
8,503,750 B2 *  8/2013  Benson ................. G06T 11/005
                                                   378/4
(Continued)

FOREIGN PATENT DOCUMENTS

KR     10-2011-0040164 A     4/2011

OTHER PUBLICATIONS

Search Report dated May 26, 2015, issued by the International Searching Authority in counterpart International Application No. PCT/KR2015/001412 (PCT/ISA/210).
(Continued)

*Primary Examiner* — Yon Couso
(74) *Attorney, Agent, or Firm* — Sughrue Mion, PLLC

(57) ABSTRACT

A computed tomography (CT) apparatus includes a reconstruction unit which reconstructs a first CT image corresponding to a field of view (FOV) by using a first sinogram acquired by a CT scan of an object; and a correction unit which acquires a second sinogram by performing forward projection on the first CT image and acquires a second CT image by using the second sinogram and a third sinogram representing a portion of the object that is not included in the
(Continued)

FOV. Thus, the CT apparatus reduces generation of image errors to thereby provide a high-quality reconstructed CT image.

11 Claims, 8 Drawing Sheets

(51) Int. Cl.
 *G06T 11/00* (2006.01)
 *A61B 6/02* (2006.01)
(52) U.S. Cl.
 CPC .......... *G06T 11/003* (2013.01); *G06T 11/006* (2013.01); *A61B 6/025* (2013.01); *A61B 6/501* (2013.01); *A61B 6/502* (2013.01); *A61B 6/503* (2013.01); *A61B 6/504* (2013.01); *A61B 6/563* (2013.01)
(58) Field of Classification Search
 CPC ......... A61B 6/503; A61B 6/501; A61B 6/461; A61B 6/504; G06T 11/006; G06T 11/003
 See application file for complete search history.

(56) References Cited

U.S. PATENT DOCUMENTS

| | | | |
|---|---|---|---|
| 2005/0105693 A1 | 5/2005 | Zhao et al. | |
| 2007/0217566 A1* | 9/2007 | Chen | G01N 23/046 378/4 |
| 2008/0152203 A1* | 6/2008 | Bal | G06T 11/008 382/131 |
| 2011/0007956 A1* | 1/2011 | Meyer | A61B 6/032 382/131 |
| 2011/0038516 A1* | 2/2011 | Koehler | A61B 6/5258 382/128 |
| 2012/0141006 A1 | 6/2012 | Koehler et al. | |
| 2012/0213327 A1 | 8/2012 | Boas | |
| 2013/0028496 A1 | 1/2013 | Panin et al. | |
| 2013/0028500 A1* | 1/2013 | Takahashi | A61B 6/032 382/132 |
| 2013/0301894 A1 | 11/2013 | Bruder et al. | |
| 2015/0146955 A1* | 5/2015 | Dong | G06T 11/006 382/131 |
| 2015/0193927 A1* | 7/2015 | Wang | G01T 1/1647 382/131 |
| 2016/0125625 A1* | 5/2016 | Kim | G06T 11/003 382/131 |

OTHER PUBLICATIONS

Written Opinion dated May 26, 2015, issued by the International Searching Authority in counterpart International Application No. PCT/KR2015/001412 (PCT/ISA/237).

* cited by examiner

[Fig. 1a]
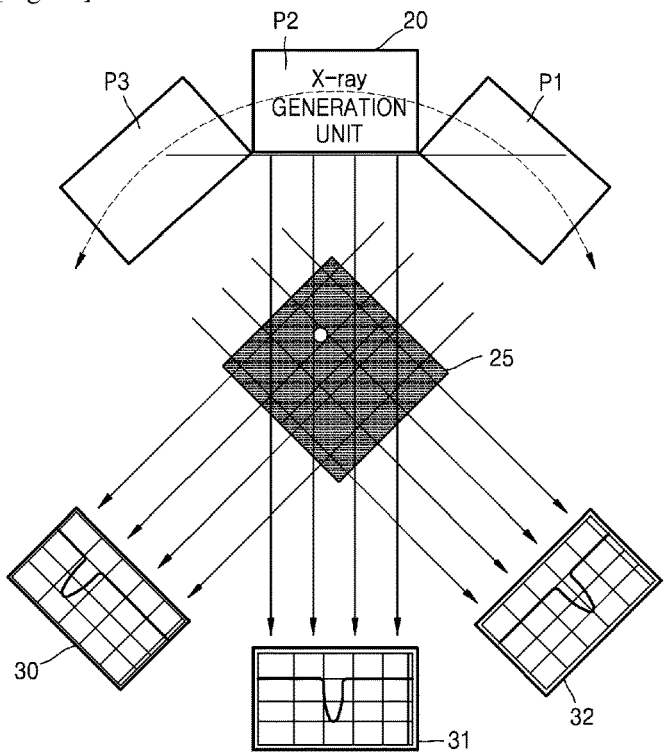
[Fig. 1b]
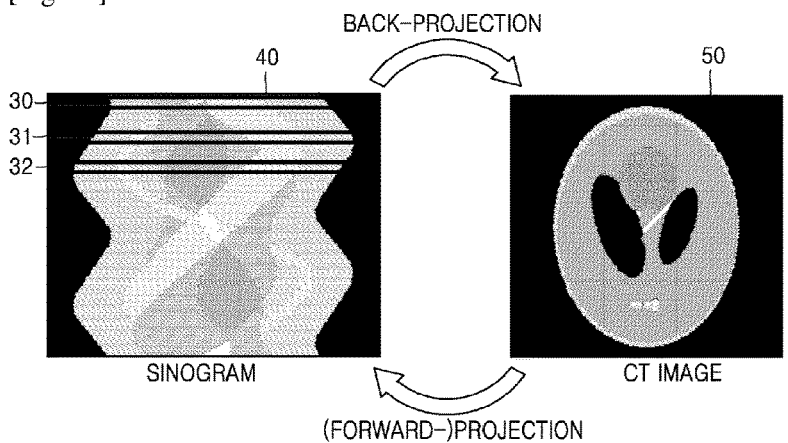
[Fig. 2]
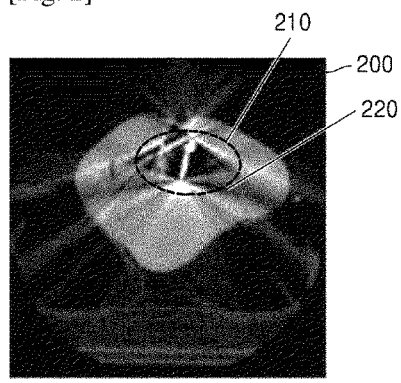

[Fig. 3]
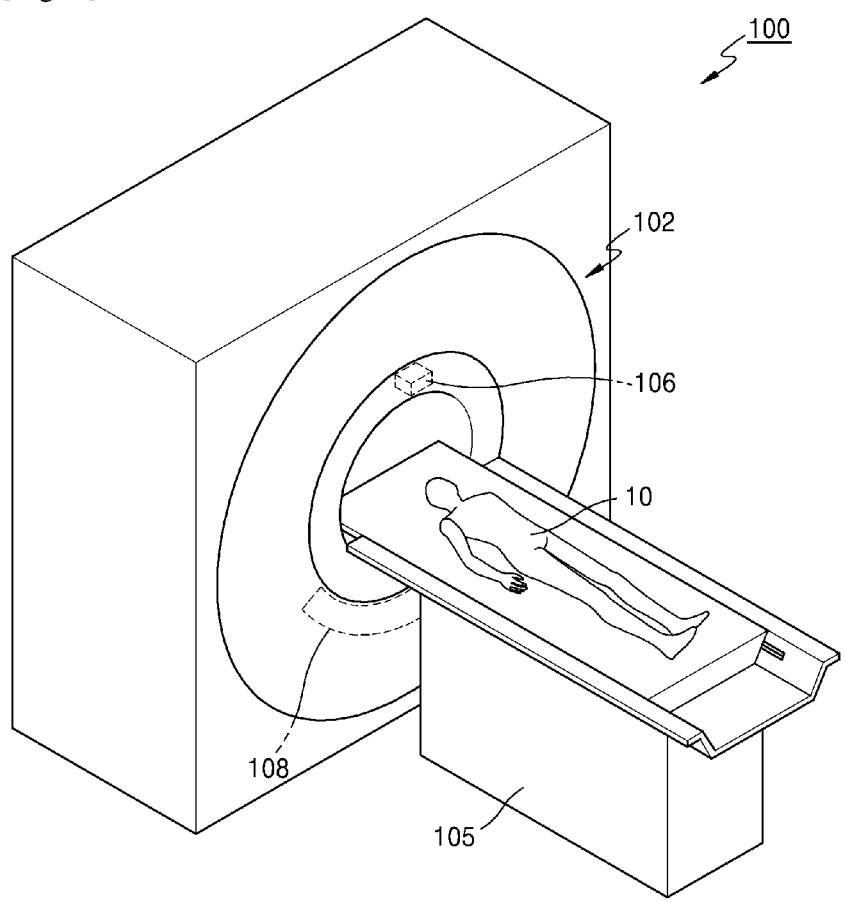

[Fig. 4]
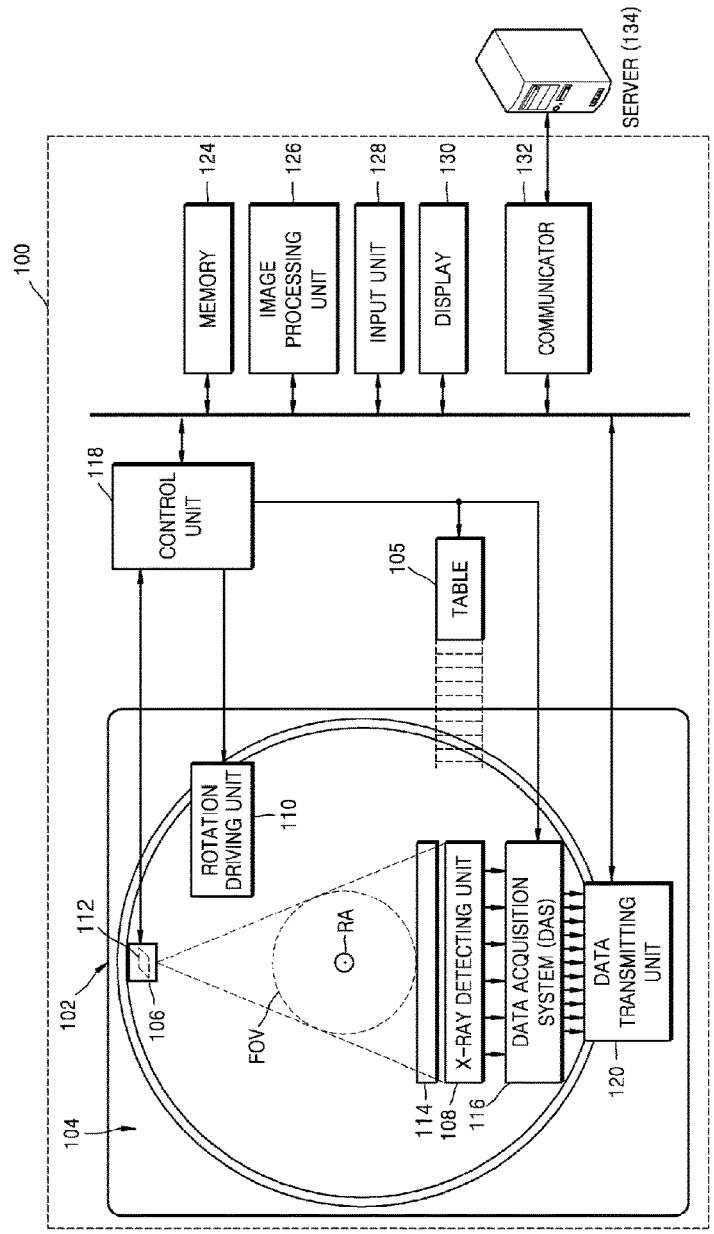
[Fig. 5]
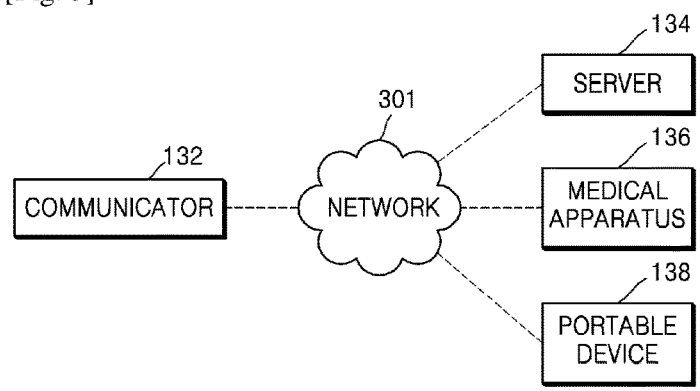

[Fig. 6]
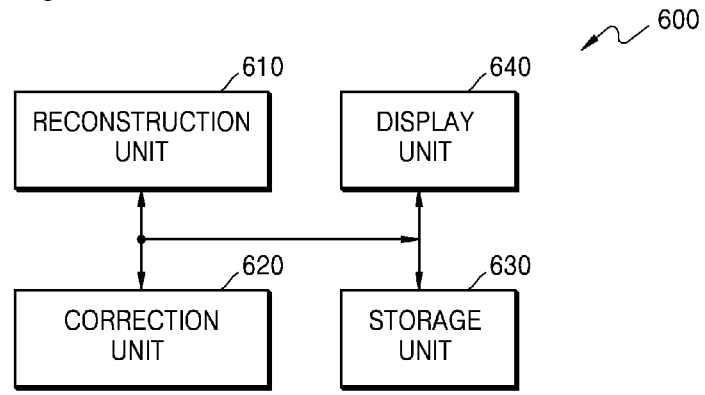
[Fig. 7a]
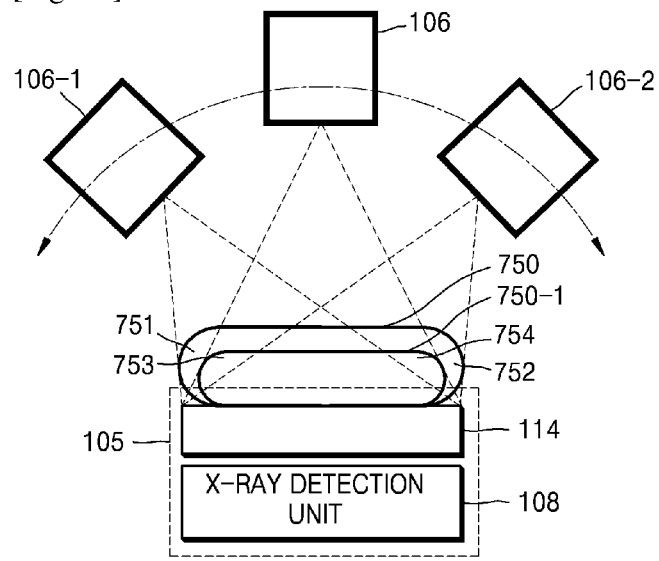
[Fig. 7b]
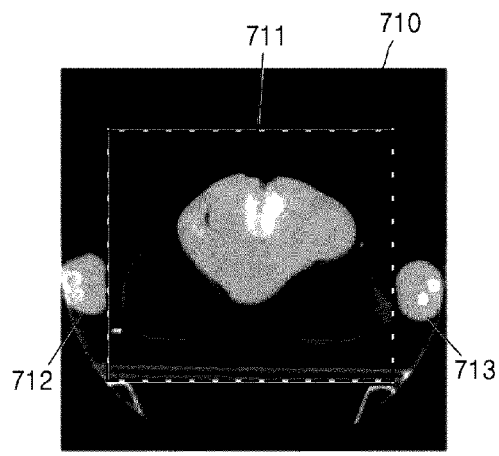

[Fig. 7c]
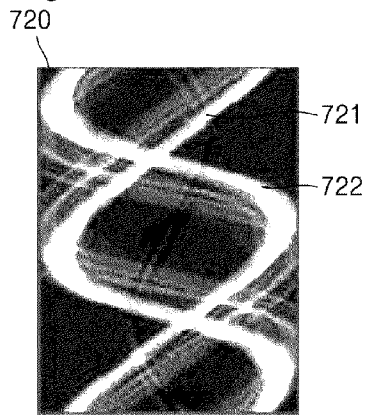
[Fig. 8]
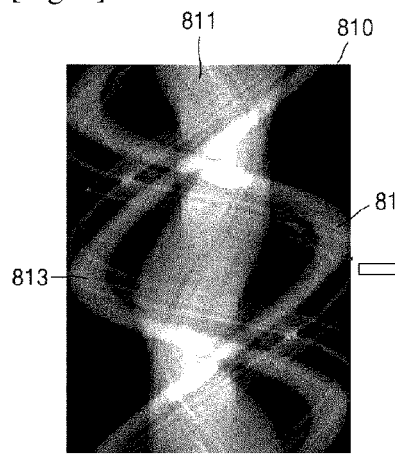 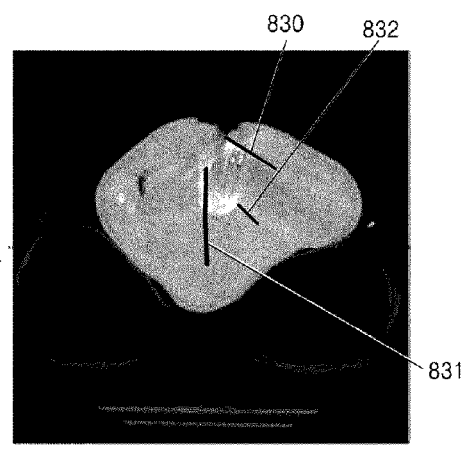
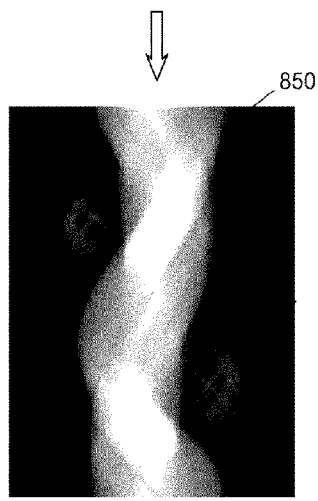

[Fig. 9]
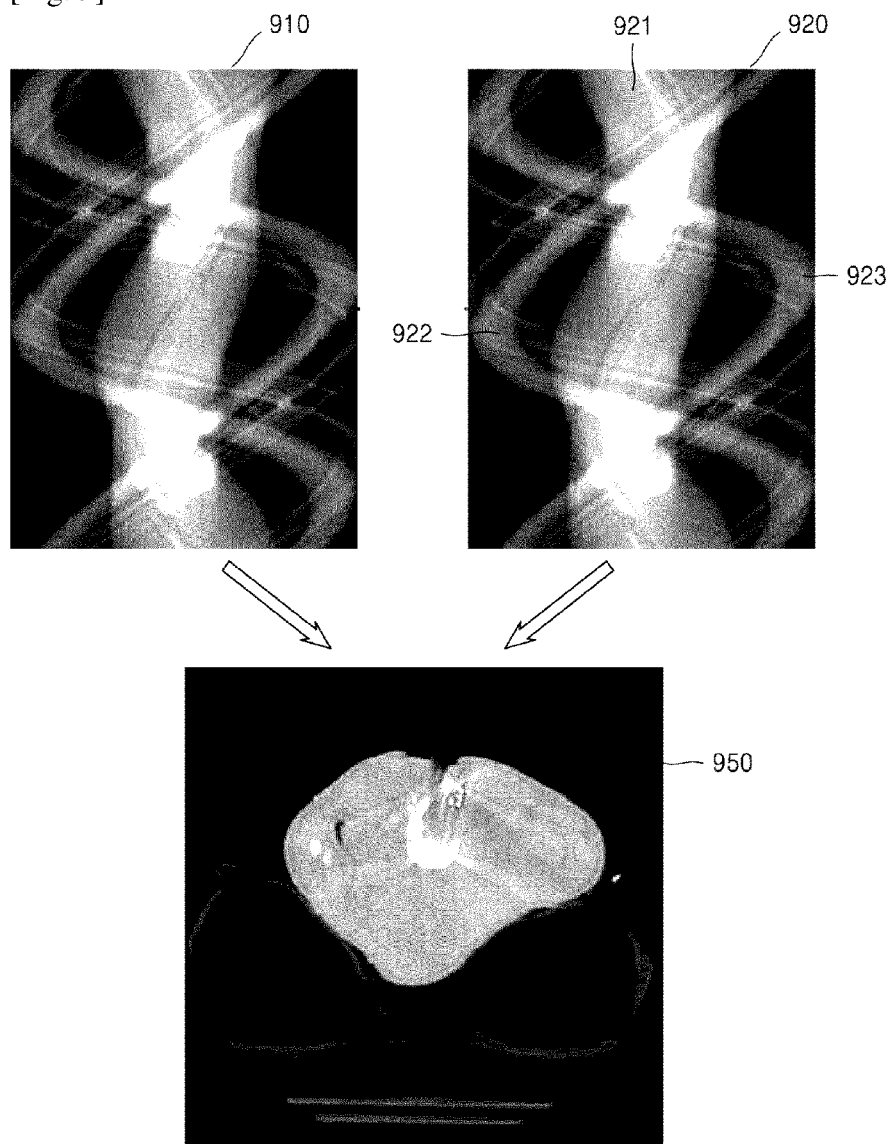
[Fig. 10]
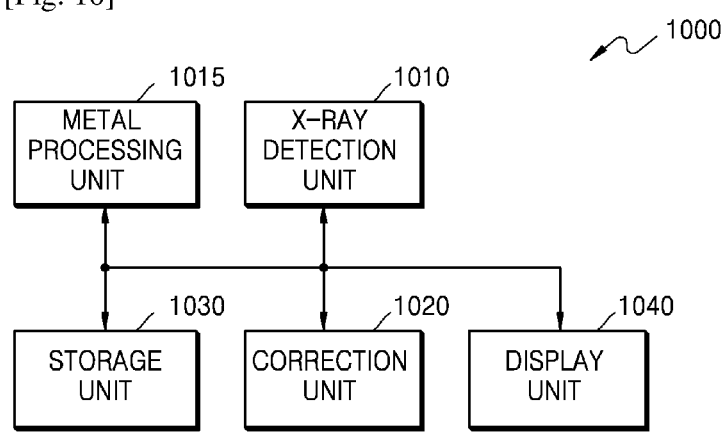

[Fig. 11]
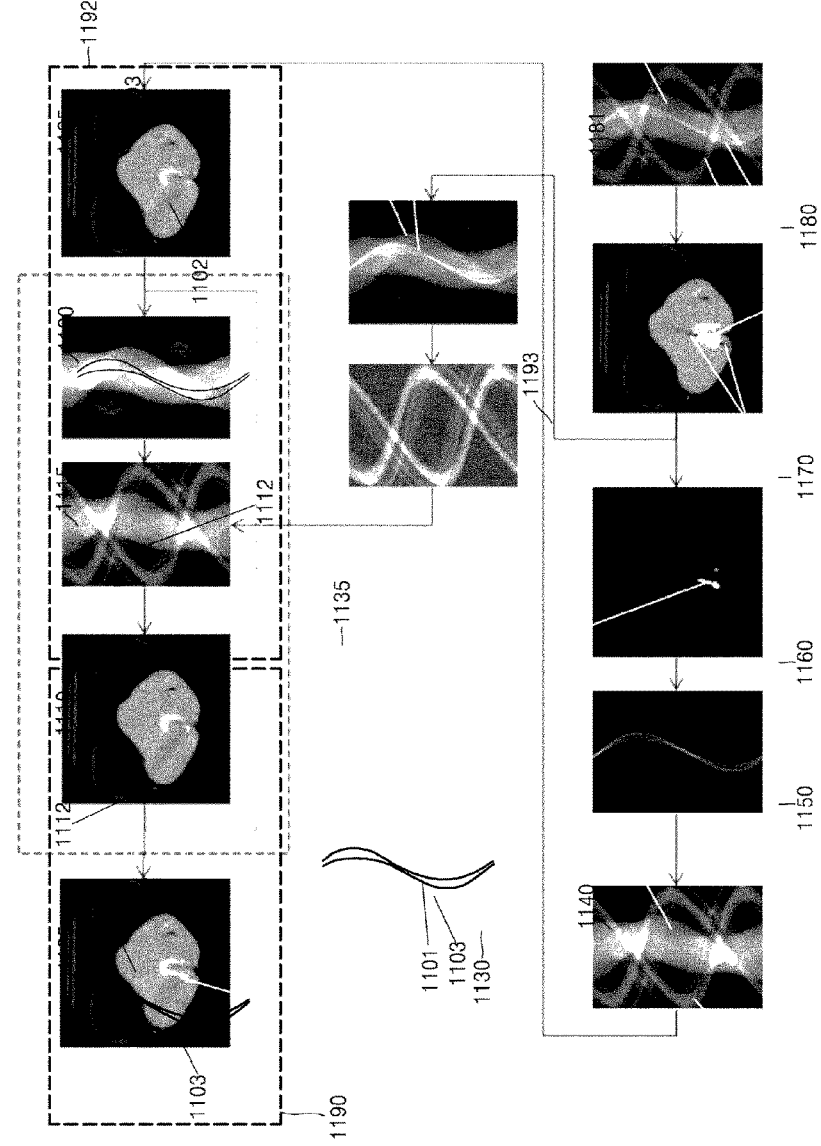
[Fig. 12]
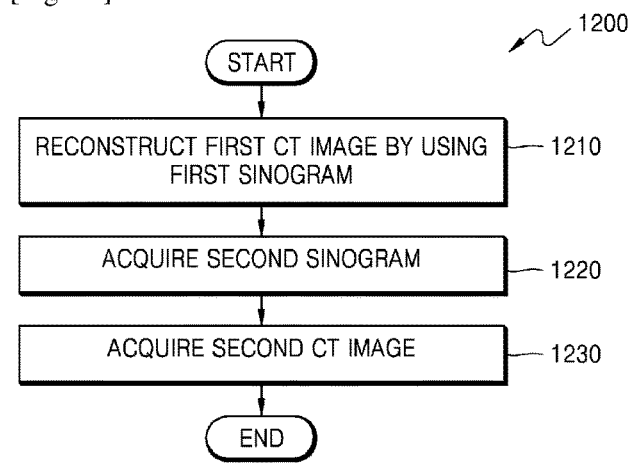

[Fig. 13]
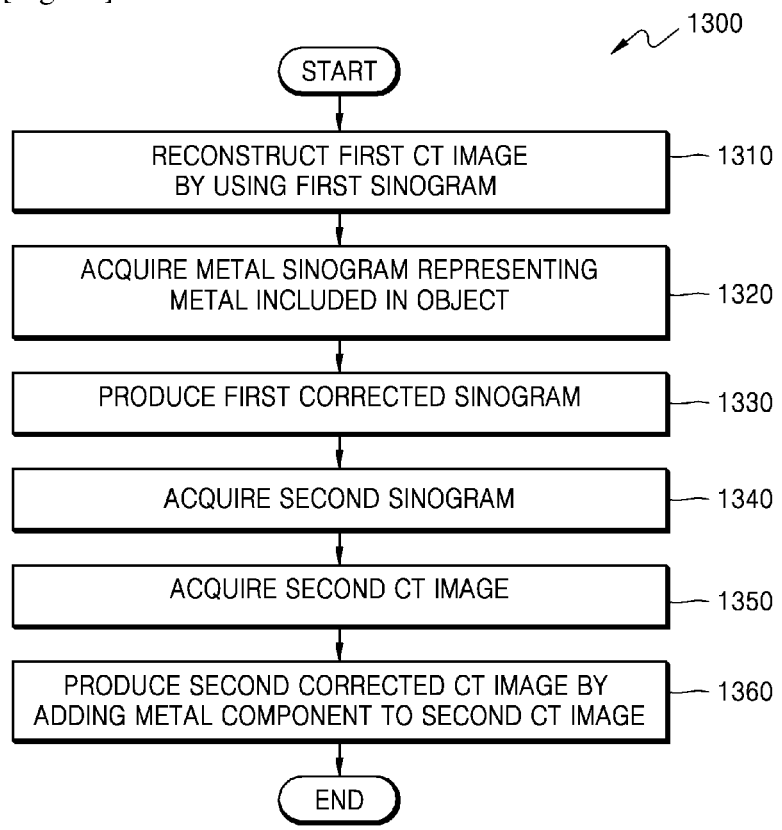

COMPUTED TOMOGRAPHY APPARATUS AND METHOD OF RECONSTRUCTING A COMPUTED TOMOGRAPHY IMAGE BY THE COMPUTED TOMOGRAPHY APPARATUS

TECHNICAL FIELD

One or more embodiments of the present invention relate to a computed tomography (CT) apparatus and a method of reconstructing a CT image by the CT apparatus.

More particularly, one or more embodiments of the present invention relate to an apparatus and method of reconstructing a CT image by using data that is acquired by a CT scan.

BACKGROUND ART

Medical imaging apparatuses are equipment for acquiring an internal structure of an object as an image. Medical image processing apparatuses are noninvasive examination apparatuses that capture images of the structural details of a human body, internal tissue thereof, and fluid flow within a human body, process the images, and show the processed images. A user such as a doctor may diagnose a health state and a disease of a patient by using a medical image output from a medical image processing apparatus.

Representative examples of apparatuses for irradiating radiation onto a patient to scan an object include computed tomography (CT).

CT apparatuses are capable of providing a cross-sectional image of an object and ex-pressing inner structures (e.g., organs such as a kidney, a lung, etc.) of the object without an overlap therebetween, compared to general X-ray apparatuses. Thus, CT apparatuses are widely used for accurately diagnosing a disease. Hereinafter, a medical image acquired by a CT apparatus is referred to as a CT image.

When a CT image is acquired, a CT scan of an object is performed using a CT apparatus to acquire raw data. The CT image is reconstructed using the acquired raw data. Raw data may be projection data acquired by projecting radiation to an object, or a sinogram that is a collection of pieces of projection data.

For example, to acquire a CT image, image reconstruction should be performed using a sinogram acquired by a CT scan. Reconstruction of a CT image will now be described in detail with reference to FIGS. 1 and 2.

FIGS. 1A and 1B are a schematic diagram and a view for describing a CT scan and CT image reconstruction.

In detail, FIG. 1A is a schematic diagram for describing a CT scan that is performed by a CT apparatus that acquires raw data while moving at intervals of a predetermined angle. FIG. 1B illustrates a sinogram acquired by a CT scan and a reconstructed CT image.

A CT apparatus generates X-rays, radiates the X-rays to an object, and detects X-rays having passed through the object by using an X-ray detector (not shown). The X-ray detector produces raw data corresponding to the detected X-rays.

In detail, referring to FIG. 1A, an X-ray generation unit 20 included in the CT apparatus radiates X-rays to an object 25. When the CT apparatus performs a CT scan, the X-ray generation unit 20 rotates around the object 25 and acquires a plurality of pieces of raw data, namely, first, second, and third raw data 30, 31, and 32, corresponding to angles at which the X-ray generation unit 20 has rotated. In detail, the X-ray detector (not shown) detects X-rays applied to the object 25 at a position P1 to thereby acquire the first raw data 30, and detects X-rays applied to the object 25 at a position P2 to thereby acquire the second raw data 31. The X-ray detector (not shown) detects X-rays applied to the object 25 at a position P3 to thereby acquire the third raw data 32. Raw data may be projection data.

Referring to FIG. 1B, a single sinogram 40 may be acquired by combining the first, second, and third raw data 30, 31, and 32 acquired while the X-ray generation unit 20 is rotating at intervals of a predetermined angle as described above with reference to FIG. 1A.

A CT image 50 is reconstructed by back-projection with respect to the sinogram 40.

When the reconstructed CT image 50 has an error, the CT apparatus or an apparatus for processing the reconstructed CT image 50 may correct the error in the reconstructed CT image 50 by acquiring a simulated sinogram via forward-projection with respect to the reconstructed CT image 50 and compensating for a difference between the simulated sinogram and the sinogram 40 acquired by a CT scan.

FIG. 2 illustrates an error existing in a reconstructed CT image.

Referring to FIG. 2, as for a CT image 200 reconstructed using the sinogram 40 acquired by a CT scan, an image error as shown in an internal region 210 of an object may be generated in cases, such as, when insufficient raw data is acquired, when a metal component exists in the object, or when information necessary for reconstruction is insufficient. In detail, the inside of the object may be wrongly expressed as shown in the internal region 210, and a black portion 220 failing to reconstruct an image pixel value may be generated inside the object.

An image error that is generated during this image reconstruction impedes medical image interpretation of a user such as a doctor.

In order for a user such as a doctor to accurately interpret the disease of a patient, a reconstructed CT image should have high accuracy. To obtain an accurate CT image, an error that may be generated in the CT image should be minimized. Accordingly, there is a demand for an apparatus and method of reconstructing a CT image while minimizing generation of an image error.

DISCLOSURE OF INVENTION

Technical Problem

To obtain an accurate CT image, an error that may be generated in the CT image should be minimized. Accordingly, there is a demand for an apparatus and method of reconstructing a CT image while minimizing generation of an image error.

Solution to Problem

One or more embodiments of the present invention include a computed tomography (CT) apparatus capable of reducing the possibility of generation of an image error within a reconstructed CT image, and a CT image reconstructing method performed by the CT apparatus.

Additional aspects will be set forth in part in the description which follows and, in part, will be apparent from the description, or may be learned by practice of the presented embodiments.

Advantageous Effects of Invention

In a CT apparatus and a CT image reconstructing method performed by the CT apparatus according to the examplary embodiments, CT image reconstruction is performed using a sinogram regarding an object not included in an FOV, leading to a reduction in the possibility of generation of errors in a reconstructed CT image. Therefore, the quality of the reconstructed CT image may increase.

BRIEF DESCRIPTION OF DRAWINGS

These and/or other aspects will become apparent and more readily appreciated from the following description of the embodiments, taken in conjunction with the accompanying drawings in which:

FIGS. 1A and 1B are a schematic diagram and a view for describing a computed tomography (CT) scan and a CT image reconstruction, respectively;

FIG. 2 illustrates an error existing in a reconstructed CT image;

FIG. 3 is a block diagram of a CT system according to an embodiment of the present invention;

FIG. 4 illustrates a structure of the CT system of FIG. 4;

FIG. 5 is a diagram illustrating an operation of the communication unit 132;

FIG. 6 is a block diagram of a CT apparatus according to an embodiment of the present invention;

FIGS. 7A, 7B, and 7C are views for describing an object not included in a field of view (FOV);

FIGS. 8 and 9 are views for describing CT image reconstruction according to an embodiment of the present invention;

FIG. 10 is a block diagram of a CT apparatus according to another embodiment of the present invention;

FIG. 11 is a view for describing CT image reconstruction according to another embodiment of the present invention;

FIG. 12 is a flow chart of a CT image reconstructing method according to an embodiment of the present invention; and FIG. 13 is a flow chart of a CT image reconstructing method according to another embodiment of the present invention.

BEST MODE FOR CARRYING OUT THE INVENTION

One or more embodiments of the present invention include a computed tomography (CT) apparatus capable of reducing the possibility of generation of an image error within a reconstructed CT image, and a CT image reconstructing method performed by the CT apparatus.

Additional aspects will be set forth in part in the description which follows and, in part, will be apparent from the description, or may be learned by practice of the presented embodiments.

According to one or more embodiments of the present invention, a CT apparatus includes a reconstruction unit which reconstructs a first CT image corresponding to a field of view (FOV) by using a first sinogram acquired by a CT scan of an object; and a correction unit which acquires a second sinogram by performing forward projection on the first CT image and acquires a second CT image by using the second sinogram and a third sinogram representing a portion of the object that is not included in the FOV.

The correction unit may acquire the second CT image, based on a fourth sinogram acquired by summing the second sinogram and the third sinogram.

The correction unit may acquire the second CT image, based on a difference between the fourth sinogram acquired by summing the second and third sinograms and the first sinogram.

The correction unit may acquire the second CT image by summing an error CT image reconstructed using the difference with the first CT image.

The correction unit may apply a weight to the error CT image reconstructed using the difference and acquire the second CT image based on the error CT image to which the weight has been applied.

The correction unit may acquire the second CT image by summing the error CT image to which the weight has been applied with the first CT image.

The correction unit may acquire the third sinogram by subtracting the second sinogram from the first sinogram.

The reconstruction unit may acquire the first CT image by performing backward projection with respect to the first sinogram.

The correction unit may model the portion of the object that is not included in the FOV and acquire the third sinogram using the modeled portion.

The correction unit may iteratively perform a process of updating the first CT image by using the second CT image and correcting an error in the first CT image by using an updated first CT image corresponding to a result of the updating.

The correction unit may acquire an updated second sinogram by performing forward projection on the updated first CT image, and may acquire an updated second CT image by using the updated second sinogram and the third sinogram.

According to one or more embodiments of the present invention, a CT apparatus includes a reconstruction unit which reconstructs a first CT image corresponding to an FOV by using a first sinogram acquired by a CT scan of an object; a metal processing unit which extracts a metal component from the first CT image, acquires a metal sinogram representing the metal component, and produces a first corrected sinogram by removing the metal component from the first sinogram by using the metal sinogram; and a correction unit which reconstructs a first corrected CT image by using the first corrected sinogram, acquires a second sinogram by performing forward projection on the first corrected CT image, acquires a second CT image by using the second sinogram and a third sinogram representing a portion of the object that is not included in the FOV, and produces a second corrected CT image by adding the extracted metal component to the second CT image.

The correction unit may acquire the second CT image, based on a fourth sinogram acquired by summing the second sinogram and the third sinogram.

The correction unit may acquire the second CT image, based on a difference between the fourth sinogram acquired by summing the second and third sinograms and the first corrected sinogram.

The correction unit may acquire the second CT image by summing an error CT image reconstructed using the difference with the first corrected CT image.

The correction unit may apply a weight to the error CT image reconstructed using the difference and acquire the second CT image based on the error CT image to which the weight has been applied.

The correction unit may acquire the second CT image by summing the error CT image to which the weight has been applied with the first corrected CT image.

The correction unit may acquire the third sinogram by subtracting the second sinogram from the first sinogram.

The reconstruction unit may acquire the first CT image by performing backward projection with respect to the first sinogram.

The reconstruction unit may acquire the first CT image by performing backward projection with respect to the first sinogram.

The correction unit may iteratively perform a process of updating the first corrected CT image by using the second CT image and correcting an error in the first CT image by using an updated first corrected CT image corresponding to a result of the updating.

According to one or more embodiments of the present invention, a CT image reconstructing method includes reconstructing a first CT image corresponding to an FOV by using a first sinogram acquired by a CT scan of an object; acquiring a second sinogram by performing forward projection on the first CT image; and acquiring a second CT image by using the second sinogram and a third sinogram representing a portion of the object that is not included in the FOV.

According to one or more embodiments of the present invention, a CT image reconstructing method includes reconstructing a first CT image corresponding to an FOV by using a first sinogram acquired by a CT scan of an object; extracting a metal component corresponding to a metal inserted into the object from the first CT image and acquiring a metal sinogram representing the extracted metal component; producing a first corrected sinogram by removing a metal component from the first sinogram by using the metal sinogram; reconstructing a first corrected CT image by using the first corrected sinogram and acquiring a second sinogram by performing forward projection on the first corrected CT image; acquiring a second CT image by using the second sinogram and a third sinogram representing a portion of the object that is not included in the FOV; and producing a second corrected CT image by adding the extracted metal component to the second CT image.

Mode for the Invention

This application claims the benefit of Korean Patent Application No. 10-2014-0016275, filed on Feb. 12, 2014, in the Korean Intellectual Property Office, the disclosure of which is incorporated herein in its entirety by reference.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. Expressions such as at least one of, when preceding a list of elements, modify the entire list of elements and do not modify the individual elements of the list.

The present invention will now be described more fully with reference to the accompanying drawings, in which exemplary embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those skilled in the art. The scope of the present invention is only defined in the claims. Throughout the specification, like reference numerals or characters refer to like elements.

The terminology used herein will now be briefly described as the present invention will be described in detail based on this terminology.

Although general terms widely used at present were selected for describing the present invention in consideration of the functions thereof, these general terms may vary according to intentions of one of ordinary skill in the art, case precedents, the advent of new technologies, and the like. Terms arbitrarily selected by the applicant of the present invention may also be used in a specific case. In this case, their meanings need to be given in the detailed description of the present invention. Hence, the terms must be defined based on their meanings and the contents of the entire specification, not by simply stating the terms.

The terms comprises and/or comprising or includes and/or including when used in this specification, specify the presence of stated elements, but do not preclude the presence or addition of one or more other elements. Also, the term 'unit' in the embodiments of the present invention means a software component or hardware components such as a field-programmable gate array (FPGA) or an application-specific integrated circuit (ASIC), and performs a specific function. However, the term 'unit' is not limited to software or hardware. The term 'unit' may be configured to be included in an addressable storage medium or to reproduce one or more processors. Thus, for example, the term 'unit' may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and 'units' may be associated with the smaller number of components and 'units', or may be divided into additional components and 'units'.

Embodiments of the present invention are described in detail herein with reference to the accompanying drawings so that this disclosure may be easily performed by one of ordinary skill in the art to which the present invention pertain. The invention may, however, be embodied in many different forms and should not be construed as being limited to the embodiments set forth herein. In the drawings, parts irrelevant to the description are omitted for simplicity of explanation.

Throughout the specification, an image may mean multi-dimensional data formed of discrete image elements (e.g., pixels in a two-dimensional (2D) image and voxels in a three-dimensional (3D) image). For example, the image may include a medical image of an object which is captured by a computed tomography (CT) apparatus.

Throughout the specification, a CT image may mean a cross-sectional image obtained by synthesizing a plurality of X-ray images that are obtained by scanning an object while a CT apparatus rotates around at least one axis with respect to the object.

Throughout the specification, a term 'object' may include a human, an animal, or a part of a human or animal. For example, the object may include organs such as the liver, the heart, the womb, the brain, a breast, the abdomen, etc., or a blood vessel. Also, the object may include a phantom. The phantom means a material having a volume that is very close to a density and effective atomic number of an organism, and may include a sphere phantom having a characteristic similar to a physical body.

Throughout the specification, a "user" may be, but is not limited thereto, a medical expert, such as a doctor, a nurse, a health care technician, or a medical imaging expert, or may be an engineer who manages medical appliances.

Since a CT system is capable of providing a cross-sectional image of an object, the CT system may express inner structures (e.g., organs such as a kidney, a lung, etc.) of the object without an overlap therebetween, compared to a general X-ray image-capturing apparatus.

The CT system may obtain a plurality of pieces of image data with a thickness not more than 2 mm for several tens to several hundreds of times per second and then may process the plurality of pieces of image data, thereby providing a relatively accurate cross-sectional image of the object. According to the related art, only a horizontal cross-sectional image of the object can be obtained, but this issue has been overcome due to various image reconstruction methods. Examples of 3D image reconstruction methods are:

A shaded surface display (SSD) method: The SSD method is an initial 3D imaging method that only displays voxels having a predetermined Hounsfield Units (HU) value.

A maximum intensity projection (MIP)/minimum intensity projection (MinIP) method: The MIP/MinIP method is a 3D imaging method that only displays voxels having the greatest or smallest HU value from among voxels that construct an image.

A volume rendering (VR) method: The VR method is an imaging method capable of adjusting a color and transmittance of voxels that construct an image, according to interest areas.

A virtual endoscopy method: This method allows an endoscopy observation in a 3D image that is reconstructed by using the VR method or the SSD method.

A multi planar reformation (MPR) method: The MPR method is used to reconstruct an image into a different cross-sectional image. A user may reconstruct an image in every desired direction.

An editing method: This method involves editing adjacent voxels so as to allow a user to easily observe an interest area in volume rendering.

A voxel of interest (VOI) method: The VOI method is used to only display a selected area in volume rendering.

A CT system 100 according to an embodiment of the present invention will now be described with reference to FIG. 3. The CT system 100 may include devices having various forms.

FIG. 3 is a block diagram of the CT system 100 according to an embodiment of the present invention. Referring to FIG. 3, the CT system 100 may include a gantry 102, a table 105, an X-ray generating unit 106, and an X-ray detecting unit 108.

The gantry 102 may include the X-ray generating unit 106 and the X-ray detecting unit 108.

An object 10 may be positioned on the table 105.

The table 105 may move in a predetermined direction (e.g., at least one of up, down, right, and left directions) during a CT scan. Also, the table 105 may tilt or rotate by a predetermined angle in a predetermined direction.

The gantry 102 may also tilt by a predetermined angle in a predetermined direction.

FIG. 4 illustrates a structure of the CT system 100.

The CT system 100 may include the gantry 102, the table 105, a control unit 118, a storage unit 124, an image processing unit 126, an input unit 128, a display unit 130, and a communication unit 132.

As described above, the object 10 may be positioned on the table 105. In the present embodiment, the table 105 may move in a predetermined direction (e.g., at least one of up, down, right, and left directions), and movement of the table 105 may be controlled by the control unit 118.

The gantry 102 may include a rotating frame 104, the X-ray generating unit 106, the X-ray detecting unit 108, a rotation driving unit 110, a data acquisition system (DAS) 116, and a data transmitting unit 120.

The gantry 102 may include the rotating frame 104 having a loop shape capable of rotating with respect to a predetermined rotation axis RA. Also, the rotating frame 104 may have a disc shape.

The rotating frame 104 may include the X-ray generating unit 106 and the X-ray detecting unit 108 that face each other so as to have predetermined field of views FOV. The rotating frame 104 may also include an anti-scatter grid 114. The anti-scatter grid 114 may be positioned between the X-ray generating unit 106 and the X-ray detecting unit 108.

In a medical imaging system, X-ray radiation that reaches a detector (or a photo-sensitive film) includes not only attenuated primary radiation that forms a valuable image but also includes scattered radiation that deteriorates a quality of an image. In order to transmit the primary radiation and to attenuate the scattered radiation, the anti-scatter grid 114 may be positioned between a patient and the detector (or the photo-sensitive film).

For example, the anti-scatter grid 114 may be formed by alternately stacking lead foil strips and an interspace material such as a solid polymer material, solid polymer, or a fiber composite material. However, formation of the anti-scatter grid 114 is not limited thereto.

The rotating frame 104 may receive a driving signal from the rotation driving unit 110 and may rotate the X-ray generating unit 106 and the X-ray detecting unit 108 at a predetermined rotation speed. The rotating frame 104 may receive the driving signal and power from the rotation driving unit 110 while the rotating frame 104 contacts the rotation driving unit 110 via a slip ring (not shown). Also, the rotating frame 104 may receive the driving signal and power from the rotation driving unit 110 via wireless communication.

The X-ray generating unit 106 may receive a voltage and current from a power distribution unit (PDU) (not shown) via a slip ring (not shown) and then a high voltage generating unit (not shown), and then may generate and emit an X-ray. When the high voltage generating unit applies a predetermined voltage (hereinafter, referred as the tube voltage) to the X-ray generating unit 106, the X-ray generating unit 106 may generate X-rays having a plurality of energy spectrums that correspond to the tube voltage.

The X-ray generated by the X-ray generating unit 106 may be emitted to have a predetermined shape by a collimator 112.

The X-ray detecting unit 108 may be positioned to face the X-ray generating unit 106. The X-ray detecting unit 108 may include a plurality of X-ray detecting devices. Each of the plurality of X-ray detecting devices may establish one channel, but one or more embodiments of the present invention are not limited thereto.

The X-ray detecting unit 108 may detect the X-ray that is generated by the X-ray generating unit 106 and that is transmitted via the object 10, and may generate an electrical signal corresponding to the intensity of the detected X-ray.

The X-ray detecting unit 108 may include an indirect-type X-ray detector for detecting radiation after converting the radiation into light, and a direct-type X-ray detector for detecting radiation after directly converting the radiation into electric charges. The indirect-type X-ray detector may use a scintillator. The direct-type X-ray detector may use a photon counting detector. The DAS 116 may be connected to the X-ray detecting unit 108. Electrical signals generated by the X-ray detecting unit 108 may be wiredly or wirelessly collected by the DAS 116. The electrical signals generated by the X-ray detecting unit 108 may be provided to an analog-to-digital converter (not shown) via an amplifier (not shown).

According to a slice thickness or the number of slices, only some of a plurality of pieces of data collected by the X-ray detecting unit 108 may be provided to the image processing unit 126 via the data transmitting unit 120, or the image processing unit 126 may select only some of the plurality of pieces of data.

Such a digital signal may be provided to the image processing unit 126 via the data transmitting unit 120. The digital signal may be wiredly or wirelessly provided to the image processing unit 126.

The control unit 118 may control an operation of each of the elements in the CT system 100. For example, the control unit 118 may control operations of the table 105, the rotation driving unit 110, the collimator 112, the DAS 116, the storage unit 124, the image processing unit 126, the input unit 128, the display unit 130, the communication unit 132, or the like.

The image processing unit 126 may receive data obtained from the DAS 116 (e.g., pure data before a processing operation), via the data transmitting unit 120, and may perform pre-processing.

The pre-processing may include a process of correcting sensitivity irregularity between channels, a process of correcting a signal loss due to a rapid decrease of signal strength or due to an X-ray absorbing material such as metal, or the like.

Data output from the image processing unit 126 may be referred as raw data or projection data. The projection data may be stored together with and scanning conditions (e.g., the tube voltage, a scanning angle, etc.) during obtainment of the projection data, in the storage unit 124.

The projection data may be a group of data values that correspond to the intensity of the X-ray that has passed through the object 10. For convenience of description, a group of a plurality of pieces of projection data that are simultaneously obtained from all channels by a same scan angle is referred as a projection data set.

The storage unit 124 may include at least one storage medium selected from among a flash memory type storage medium, a hard disk type storage medium, a multimedia card micro type storage medium, card type memory (for example, a secure digital (SD) or extreme digital (XD) memory), random access memory (RAM), static random access memory (SRAM), read-only memory (ROM), electrically erasable programmable ROM (EEPROM), programmable ROM (PROM), magnetic memory, a magnetic disk, and an optical disk.

The image processing unit 126 may reconstruct a cross-sectional image with respect to the object 10 by using the projection data set. The cross-sectional image may be a 3D image. In other words, the image processing unit 126 may reconstruct a 3D image of the object 10 by using a cone beam reconstruction method or the like, based on the obtained projection data set.

The input unit 128 may receive an external input with respect to an X-ray tomography imaging condition, an image processing condition, or the like. For example, the X-ray tomography imaging condition may include a plurality of tube voltages, energy value setting with respect to a plurality of X-rays, selection of an image-capturing protocol, selection of an image reconstruction method, setting of a FOV area, the number of slices, a slice thickness, setting of image post-processing parameters, or the like. The image processing condition may include resolution of an image, attenuation coefficient setting with respect to the image, setting of an image combining ratio, or the like.

The input unit 128 may include a device for receiving a predetermined input from an external source. For example, the input unit 128 may include a microphone, a keyboard, a mouse, a joystick, a touch pad, a touch pen, a voice recognition device, a gesture recognition device, or the like.

The display unit 130 may display an X-ray tomography image reconstructed by the image processing unit 126.

Exchanges of data, power, or the like between the aforementioned elements may be performed by at least one of wired communication, wireless communication, and optical communication.

The communication unit 132 may perform communication with an external device, an external medical apparatus, or the like via a server 134 or the like. The communication will now be described with reference to FIG. 3.

FIG. 5 is a diagram illustrating an operation of the communication unit 132.

The communication unit 132 may be wiredly or wirelessly connected to a network 301 and thus may perform communication with an external device, such as the server 134, an external medical apparatus 136, or a portable device 138. The communication unit 132 may exchange data with a hospital server or other medical apparatuses in a hospital connected via a Picture Archiving and Communication System (PACS).

Also, the communication unit 132 may perform data communication with the external device or the like, according to a Digital Imaging and Communications in Medicine (DICOM) standard.

The communication unit 132 may transmit and receive data related to diagnosing the object 10, via the network 301. Also, the communication unit 132 may transmit and receive a medical image obtained from the medical apparatus 136 such as a magnetic resonance imaging (MRI) apparatus, an X-ray apparatus, or the like.

Furthermore, the communication unit 132 may receive a diagnosis history or a medical treatment schedule about a patient from the server 134 and utilize the received diagnosis history or medical treatment schedule to diagnose the patient. The communication unit 132 may perform data communication with not only the server 134 or the medical apparatus 136 in a hospital but also with the portable device 138 of a user or patient.

The communication unit 132 may transmit information about a device error, information about a quality control status, or the like to a system manager or a service manager via the network 301, and may receive a feedback corresponding to the information.

FIG. 6 is a block diagram of a CT apparatus 600 according to an embodiment of the present invention.

Referring to FIG. 6, the CT apparatus 600 includes a reconstruction unit 610 and a correction unit 620. The CT apparatus 600 may further include at least one of a storage unit 630 and a display unit 640.

The CT apparatus 600 may be included in the CT system 100 described above with reference to FIGS. 3 and 4. Alternatively, the CT apparatus 600 may be included in the medical apparatus 136 or the portable device 138 of FIG. 5 and may be connected to the CT system 100 to operate.

When the CT apparatus 600 is included in the CT system 100, the reconstruction unit 610 and the correction unit 620 may be included in the image processing unit 126 of FIG. 4. The storage unit 630 and the display unit 640 of FIG. 6 may be the same as the storage unit 124 and the display unit 130 of FIG. 4, respectively.

The reconstruction unit 610 may reconstruct a first CT image corresponding to an FOV by using a first sinogram acquired by a CT scan of an object. The FOV is determined by the X-ray generating unit 106 and the X-ray detecting unit 108.

In detail, while the rotating frame 104 of the CT system 100 is rotating the X-ray generating unit 106 and the X-ray detecting unit 108 at a predetermined rotation speed, a CT scan is performed, and thus a plurality of pieces of projection data may be acquired. The first sinogram may be acquired using the plurality of pieces of projection data.

The reconstruction unit 610 may directly receive the first sinogram acquired by the CT system 100. Alternatively, the reconstruction unit 610 may receive the plurality of pieces of projection data acquired by the CT system 100 and generate the first sinogram by using the received plurality of pieces of projection data.

The first sinogram is a sinogram produced directly from pieces of raw data acquired by a CT scan. The reconstruction unit 610 transforms the first sinogram to reconstruct the first CT image. In detail, the reconstruction unit 610 may acquire the first CT image by performing a radon transform on the first sinogram.

The correction unit 620 acquires a second sinogram by performing forward projection on the first CT image.

For example, the correction unit 620 may acquire the second sinogram by performing an inverse radon transform on the first CT image. A second sinogram is not a sinogram generated using raw data acquired by a CT scan, but a sinogram simulated using a CT image.

The correction unit 620 also acquires a second CT image by using the second sinogram and a third sinogram representing a portion of the object that is not included in the FOV. The second CT image is a CT image obtained by correcting an error generated in the first CT image. The third sinogram will now be described in more detail with reference to FIG. 7.

FIGS. 7A, 7B, and 7C are views for describing an object not included in an FOV.

Referring to FIG. 7A, the X-ray generation unit 106 radiates X rays toward an object 750 located on the table 105. X-rays that have passed through the object 750 are detected by the X-ray detection unit 108 via the anti-scatter grid 114.

The X-ray generating unit 106 and the X-ray detecting unit 108 may be formed to have a predetermined FOV. When the size of an object is big or the object is mislocated on the table 105, the entire object may not be included in the FOV determined by the X-ray generating unit 106 and the X-ray detecting unit 108. In other words, portions 751 and 752 of the object 750 may not be included in the FOV, and the X-ray detection unit 108 may fail to detect X-rays that have passed through the portions 751 and 752 of the object 750.

In addition, even when an object 750-1 is entirely included in an FOV determined by the X-ray generation unit 106 located in front of the object 750-1, a portion 754 or 753 of the object 750-1 may not be included in an FOV determined by an X-ray generation unit 106-1 or 106-2 located on the left or right side of the object 750-1. In this case, the X-ray detection unit 108 may fail to detect X-rays that have passed through the portions 753 and 754 of the object 750-1, because of the positions of the X-ray generation units 106-1 and 106-2.

FIG. 7B illustrates a CT image 710 for describing a portion of the object 711 that is included in a FOV and the portions 712 and 713 of the object 750 that are not included in the FOV. In detail, the portions 712 and 713 of the object 750 that are not included in the FOV illustrated in the FIG. 7B correspond to the portions 751 and 752 of the object 750 illustrated in the FIG. 7A.

Referring to FIG. 7B, the CT image 710 includes both a CT image 711 representing an object included in a FOV and objects 712 and 713 not included in the FOV. For example, when the object 750 is the abdomen of a patient, the CT image 711 may be a cross-section of the abdomen. The portions 712 and 713 of the object not included in the FOV may be a portion of the CT image 710 including both arms of the patient, except for the CT image 711 included in the FOV.

In FIG. 7B, sizes of the objects 712 and 713 not included in the FOV may increase or decrease according to positions (or rotation angles) of the X-ray generation unit 106. For example, when the X-ray generation unit 106-2 radiates X-rays to the object 750-1, the portion 753 of the left end portion of the object is not included in the FOV determined by the X-ray generation unit 106-2. On the other hand, when the X-ray generation unit 106 radiates X-rays to the object 750-1, the entire portion of the object 750-1 is included in the FOV determined by the X-ray generation unit 106. When the X-ray generation unit 106-1 radiates X-rays to the object 750-1, the portion 754 of the object 750-1 may be not included in the FOV determined by the X-ray generation unit 106-1.

As described above, a portion of an object not included in a FOV may or may not exist according to positions or rotation angles of the X-ray generation unit 106.

FIG. 7C illustrates a third sinogram 720.

The third sinogram 720 includes components 721 and 722 representing portions of an object that are not included in an FOV. Herein, the components 721 and 722 represent sinograms produced by portions of the object that are not included in the FOV, such as the portions 712 and 713.

As illustrated in FIG. 7C, the portions 751, 752, 753, and 754, which are not included in an FOV as described above with reference to FIG. 7A, are expressed as the components 721 and 722 of the third sinogram 720.

The CT apparatus 600 corrects an error in a CT image by using a third sinogram which corresponds to sinograms to the objects 712 and 713 not included in the FOV. Error correction of a reconstructed CT image will be described in detail with reference to FIGS. 8 and 9.

The storage unit 630 may store a plurality of pieces of data acquired during a CT scan. In detail, the storage unit 630 may store projection data, which is row data, or sinograms. The storage unit 630 may also store various kinds of data, programs, and the like necessary for reconstructing a CT image, and may store a finally-reconstructed CT image.

The storage unit 630 may include at least one storage medium selected from among a flash memory type storage medium, a hard disk type storage medium, a multimedia card micro type storage medium, card type memory (for example, a secure digital (SD) or extreme digital (XD) memory), random access memory (RAM), static random access memory (SRAM), read-only memory (ROM), electrically erasable programmable ROM (EEPROM), programmable ROM (PROM), magnetic memory, a magnetic disk, and an optical disk.

The display unit 640 may display the reconstructed CT image to a user. In detail, the display unit 640 may display at least one of the first sinogram, the first CT image, the second sinogram, the third sinogram, and the second CT image which are produced during CT image reconstruction. The display unit 640 may also sequentially display CT images that are produced during a CT scan. For example, the display unit 640 may display the first CT image and then display the second CT image obtained by correcting an error in the first CT image.

FIG. 8 is a view for describing CT image reconstruction according to an embodiment of the present invention.

FIG. 9 is another view for describing the CT image reconstruction according to an embodiment of the present invention.

Referring to FIG. 8, the reconstruction unit 610 acquires a first sinogram 810 produced by X-rays detected during a CT scan. In the first sinogram 810 of FIG. 8, a component 811 is a sinogram component corresponding to an object included in an FOV, and components 812 and 813 are sinogram components corresponding to at least one portion of the object not included in a FOV.

The reconstruction unit 610 reconstructs a first CT image 830 by performing back-projection with respect to the first sinogram 810. The first CT image 830 is an image representing the object included in the FOV. Image errors 831 and 832, such as black blurring, may exist within the first CT image 830.

The correction unit 620 produces a second sinogram 850 by performing forward projection on the first CT image 830. The second sinogram 850 is not a sinogram generated by radiating X-rays to an object and detecting the X-rays, but a sinogram simulated using a CT image.

Referring to FIG. 9, the correction unit 620 may acquire a second CT image 950, based on a fourth sinogram 910 acquired by summing the second sinogram 850 with the third sinogram 720 of FIG. 7C, which represents a portion of an object not included in a FOV. In detail, the correction unit 620 reconstructs the second CT image 950 by performing back-projection with respect to the fourth sinogram 910. Referring to FIG. 9, it can be seen that the second CT image 950 reconstructed using the fourth sinogram 910 does not include the errors 831 and 832 existing in the first CT image 830.

The fourth sinogram 910 may be produced by adding the third sinogram 720 to the second sinogram 850.

The third sinogram 720 may be produced by subtracting the second sinogram 850 from the first sinogram 810.

Alternatively, the third sinogram 720 may be produced using a modeled portion of an object that is not included in an FOV. For example, when an abdomen CT scan is performed, the positions and sizes of arms of a patient which are included in an abdominal cross-section but are not included in an FOV are modeled. Sinograms corresponding to the modeled arms may be produced.

In detail, virtual sinograms corresponding to the modeled arms may be produced, or sinograms may be produced by an actual CT scan of the modeled arms. Modeling of a portion of an object not included in an FOV may be performed in consideration of the gender, age, body size, or the like of a patient who is the object. For example, an arm of a patient may be modeled with average values of the sizes and thickness of the bones of arms of patients, according to the gender and age of the patient.

The correction unit 620 may acquire the second CT image 950 by correcting the first CT image 830 based on a difference between the fourth sinogram 910, which is a sum of the second sinogram 850 and the third sinogram 720, and a first sinogram 920. The first sinogram 920 of FIG. 9 is the same as the first sinogram 810 of FIG. 8. The difference between the fourth sinogram 910 and the first sinogram 920 will now be referred to as a difference value. The difference value has a sinogram form.

In detail, the correction unit 620 may acquire the second CT image 950 by summing the first CT image 830 with an error CT image reconstructed using the difference value. In detail, the error CT image is produced by performing backward-projection on the difference value, and the produced error CT image is added to the first CT image 830. The addition may be performed using various image addition methods, such as a sum of square, image composition, and the like.

The correction unit 620 may apply a weight to the error CT image reconstructed using the difference value and correct an error in the first CT image based on the error CT image to which the weight has been applied. In detail, the correction unit 620 may produce the second CT image by adding the error CT image to which the weight has been applied to the first CT image.

For example, when a signal value of a predetermined point on the first CT image is a, a signal value of a predetermined point on the error CT image is b, and the weight is set to be 0.5, a signal value of a predetermined point on the second CT image may be a +0.5b. The weight may be received from a user or may be set to be a predetermined value by the correction unit 620.

The correction unit 620 may perform iterative reconstruction in which the second CT image acquisition described above with reference to FIGS. 8 and 9 is repeatedly performed, thereby repeatedly addressing an error within an image.

In detail, the correction unit 620 may iteratively perform a process of updating the first CT image 830 by using the second CT image 950 and correcting an error by using an updated first CT image corresponding to a result of the updating. In other words, the correction unit 620 receives the updated first CT image as the second CT image 950. In addition, the correction unit 620 acquires an updated second sinogram by performing forward-projection on the updated first CT image, and acquires an updated second CT image by using the updated second sinogram and the third sinogram.

FIG. 10 is a block diagram of a CT apparatus 1000 according to another embodiment of the present invention.

The CT apparatus 1000 includes a reconstruction unit 1010, a correction unit 1020, and a metal processing unit 1015. The CT apparatus 1000 may further include at least one of a storage unit 1030 and a display unit 1040.

The CT apparatus 1000 may be included in the CT system 100 described above with reference to FIGS. 3 and 4. Alternatively, the CT apparatus 1000 may be included in the medical apparatus 136 or the portable device 138 of FIG. 5 and may be connected to the CT system 100 to operate.

When the CT apparatus 1000 is included in the CT system 100, the reconstruction unit 1010, the correction unit 1020, and the metal processing unit 1015 may be included in the image processing unit 126 of FIG. 4. The storage unit 1030 and the display unit 1040 of FIG. 10 may be the same as the storage unit 124 and the display unit 130 of FIG. 4, respectively.

The reconstruction unit 1010 may reconstruct a first CT image corresponding to an FOV by using a first sinogram acquired by a CT scan of an object. The reconstruction unit 1010 is the same as the reconstruction unit 610 of FIG. 6, and thus a detailed description thereof will be omitted.

The metal processing unit 1015 extracts a metal from the first CT image and acquires a metal sinogram representing the metal. In addition, the metal processing unit 1015 produces a first corrected sinogram by excluding a metal component from the first sinogram by using the metal sinogram.

The correction unit 1020 reconstructs a first corrected CT image by using the first corrected sinogram and acquires a second sinogram by performing forward-projection on the first corrected CT image. The correction unit 1020 also acquires a second CT image by using the second sinogram and a third sinogram representing a portion of the object that is not included in the FOV. The correction unit 1020 also produces a second corrected CT image by adding the extracted metal to the second CT image.

The storage unit 1030 may store a plurality of pieces of data acquired during a CT scan.

The display unit 1040 may display the reconstructed CT image to a user. In detail, the display unit 1040 may display at least one of selected from the first reconstructed image, the first corrected reconstructed image, the second reconstructed image, and the second corrected reconstructed image.

The storage unit 1030 and the display unit 1040 are the same as the storage unit 630 and the display unit 640 of FIG. 6, and thus a detailed description thereof will be omitted.

A detailed operation of the CT apparatus 1000 will now be described in detail with reference to FIG. 11.

FIG. 11 is a view for describing CT image reconstruction according to another embodiment of the present invention.

Referring to FIG. 11, a portion 1190 represents an operation of the reconstruction unit 1010, a portion 1192 represents an operation of the metal processing unit 1015, and a portion 1193 represents an operation of the correction unit 1020.

While the rotating frame 104 of the CT system 100 is rotating the X-ray generating unit 106 and the X-ray detecting unit 108 at a predetermined rotation speed, a CT scan is performed, and thus a plurality of pieces of projection data may be acquired. A first sinogram may be acquired using the plurality of pieces of projection data.

Referring to FIG. 11, the reconstruction unit 1010 may directly receive a first sinogram 1105 acquired by the CT system 100. Alternatively, the reconstruction unit 1010 may receive the plurality of pieces of projection data acquired by the CT system 100 and generate the first sinogram 1105 by using the received plurality of pieces of projection data.

The first sinogram 1105 is a sinogram produced directly from pieces of raw data acquired by a CT scan. The reconstruction unit 1010 may acquire a first CT image 1110 by performing a radon transform on the first sinogram 1105.

Due to a surgical operation for treatment, a metal may be inserted into the body of a patient. In this case, an image error may be generated within a CT image acquired by a CT scan, due to the metal inserted into the body.

Due to the metal existing in the patient, which is an object, a metal component 1101 is included in the first sinogram 1105. The first sinogram 1105 also includes a component 1103 corresponding to an object included in an FOV. As described above with reference to FIG. 7, the first sinogram 1105 may also include a component 1102 corresponding to portions of an object that are not included in the FOV, for example, the arms.

In the first CT image 1110 acquired by backward-projection of the first sinogram 1105, an error 1111 in which a region around a metal component 1112 looks black may be generated due to the metal component 1112. To remove the error 1111, the correction unit 1020 removes the metal component 1101 from the first sinogram 1105 and then performs second CT image reconstruction.

The metal processing unit 1015 extracts the metal component 1112 from the first CT image 1110. For example, the metal component extraction may be performed using a brightness value of an image signal in the first CT image 1110. In detail, a metal component is displayed brightly as illustrated in FIG. 11, and, when a bright region is extracted, the metal component 1112 may be extracted as shown in a metal image 1115. According to various other methods of extracting an object from an image, the metal component 1112 may be extracted.

A metal sinogram 1120 is produced using the metal image 1115. In detail, a metal sinogram 1120 may be produced by forward-projecting the metal image 1115.

Then, a first corrected sinogram 1125 is produced by excluding the metal sinogram 1120 from the first sinogram 1105. For example, the first corrected sinogram 1125 may be produced by removing the metal sinogram 1120 from the first sinogram 1105 and interpolating portion of the first sinogram 1105 from which the metal component 1101 has been removed.

Accordingly, the first corrected sinogram 1125 includes the component 1103 corresponding to the object included in the FOV and the component 1102 corresponding to the object not included in the FOV, and does not include the metal component 1101.

A third sinogram 1135 representing the object not included in the FOV may be acquired by subtracting a sinogram 1130 acquired by forward-projecting the first CT image 1110 from the first sinogram 1105.

Alternatively, the third sinogram 1135 may be produced using a modeled portion of an object that is not included in an FOV.

The third sinogram 1135 may be produced in the same manner as the manner in which the third sinogram 720 of FIG. 7 is produced. Thus, a repeated description thereof will be omitted.

Then, the correction unit 1020 reconstructs a first corrected CT image 1140 by backward-projecting the first corrected sinogram 1125. In addition, the correction unit 1020 acquires a second sinogram 1150 by forward-projecting the first corrected CT image 1140.

The correction unit 1020 may acquire a second CT image 1170, based on a fourth sinogram 1160 acquired by summing the second sinogram 1150 with the third sinogram 1135, which represents the object not included in the FOV. In detail, the correction unit 1020 may produce the second CT image 1170 by performing backward projection with respect to the fourth sinogram 1160.

Alternatively, the correction unit 1020 may acquire the second CT image 1170, based on a difference between the fourth sinogram 1160, which is a sum of the second sinogram 1150 and the third sinogram 1135, and the first sinogram 1105. The difference between the fourth sinogram 1160 and the first sinogram 1105 will now be referred to as a difference value. The difference value has a sinogram form.

In detail, the correction unit 1020 may acquire the second CT image 1170 by summing the first corrected CT image 1140 with an error CT image reconstructed using the difference value. In detail, the error CT image is produced by backward-projecting the difference, and the produced error CT image is added to the first corrected CT image 1140. The addition may be performed using various image addition methods, such as a sum of square, image composition, and the like.

The correction unit 1020 may apply a weight to the error CT image reconstructed using the difference value and correct an error in the first corrected CT image 1140 based on the error CT image to which the weight has been applied. In detail, the correction unit 1020 may produce the second CT image 1170 by adding the error CT image to which the weight has been applied to the first corrected CT image 1140.

The correction unit 1020 also produces a second corrected CT image 1180 by adding a metal component 1181 to the second CT image 1170. The metal component 1181 is the same as the metal component 1112 extracted from the first CT image 110.

Moreover, the correction unit 1020 may perform iterative reconstruction in which the above-described acquisition of the second CT image 1170 is repeatedly performed, thereby repeatedly addressing an error within an image.

In detail, the correction unit 1020 may iteratively perform a process of updating the first corrected CT image 1140 by using the second CT image 1170 and correcting an error by using an updated first corrected CT image corresponding to a result of the updating. In other words, the correction unit 1020 receives the second CT image 1170 as the updated first corrected CT image. In addition, the correction unit 1020 acquires an updated second sinogram by performing forward-projection on the updated first corrected CT image, and acquires an updated second CT image by using the updated second sinogram and the third sinogram.

FIG. 12 is a flow chart of a CT image reconstructing method 1200 according to an embodiment of the present invention.

The CT image reconstructing method 1200 may be performed by the CT apparatus 600 described above with reference to FIGS. 6-9. Operations of the CT image reconstructing method 1200 include the same technical spirits as those of the above-described operations of the CT apparatus 600. A repeated description of matters described above with reference to FIGS. 6-9 is omitted herein.

In operation 1210, a first CT image corresponding to an FOV is reconstructed using a first sinogram acquired by a CT scan of an object. The operation 1210 may be performed by the reconstruction unit 610.

In operation 1220, a second sinogram is acquired by performing forward projection on the first CT image acquired in operation 1210. The operation 1220 may be performed by the correction unit 620.

In operation 1230, a second CT image is acquired using the second sinogram and a third sinogram representing a portion of the object that is not included in the FOV. The operation 1230 may be performed by the correction unit 620.

FIG. 13 is a flow chart of a CT image reconstructing method 1300 according to another embodiment of the present invention.

The CT image reconstructing method 1300 may be performed by the CT apparatus 1000 described above with reference to FIGS. 10-11. Operations of the CT image reconstructing method 1300 include the same technical spirits as those of the above-described operations of the CT apparatus 1000. A repeated description of matters described above with reference to FIGS. 10 and 11 is omitted herein.

In operation 1310, a first CT image corresponding to an FOV is reconstructed using a first sinogram acquired by a CT scan of an object. The operation 1310 may be performed by the reconstruction unit 1010.

In operation 1320, a metal is extracted from the first CT image acquired in operation 1310, and a metal sinogram representing the extracted metal is acquired. The operation 1320 may be performed by the metal processing unit 1015.

In operation 1330, a first corrected sinogram is produced by excluding a metal component from the first sinogram by using the metal sinogram. The operation 1330 may be performed by the metal processing unit 1015.

In operation 1340, a first corrected CT image is reconstructed using the first corrected sinogram produced in operation 1330, and a second sinogram is acquired by performing forward projection on the first corrected CT image. The operation 1340 may be performed by the correction unit 1020.

In operation 1350, a second CT image is acquired using the second sinogram and a third sinogram representing a portion of the object that is not included in the FOV. The operation 1350 may be performed by the correction unit 1020.

In operation 1360, a second corrected CT image is produced by adding the extracted metal to the second CT image. The operation 1360 may be performed by the correction unit 1020.

As described above, in a CT apparatus and a CT image reconstructing method performed by the CT apparatus according to the one or more of the above embodiments of the present invention, CT image reconstruction is performed using a sinogram regarding an object not included in an FOV, leading to a reduction in the possibility of generation of errors in a reconstructed CT image. Therefore, the quality of the reconstructed CT image may increase.

The embodiments of the present invention can be written as computer programs and can be implemented in general-use digital computers that execute the programs using a computer readable recording medium.

Examples of the computer readable recording medium include magnetic storage media (e.g., ROM, floppy disks, hard disks, etc.), optical recording media (e.g., CD-ROMs, or DVDs), etc.

The exemplary embodiments should be considered in descriptive sense only and not for purposes of limitation. Descriptions of features or aspects within each embodiment should typically be considered as available for other similar features or aspects in other embodiments.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A computed tomography (CT) apparatus comprising:
   an image processor configured to:
      perform back-projection on a first sinogram that is acquired by a CT scan of an object, to reconstruct a first CT image corresponding to a field of view (FOV);
      perform forward projection on the first CT image, to acquire a second sinogram representing a first portion of the object that is included in the FOV;
      sum the second sinogram and a third sinogram representing a second portion of the object that is not included in the FOV, to acquire a fourth sinogram; and
      correct the first CT image, based on a difference between the fourth sinogram and the first sinogram, to acquire a second CT image.

2. The CT apparatus of claim 1, wherein the image processor is further configured to:
   perform back-projection on the difference between the fourth sinogram and the first sinogram, to reconstruct an error CT image; and
   sum the error CT image and the first CT image, to acquire the second CT image.

3. The CT apparatus of claim 1, wherein the image processor is further configured to:
perform back-projection on the difference between the fourth sinogram and the first sinogram, to reconstruct an error CT image;
apply a weight to the error CT image; and
acquire the second CT image, based on the error CT image to which the weight is applied.

4. The CT apparatus of claim 3, wherein the image processor is further configured to sum the first CT image and the error CT image to which the weight is applied, to acquire the second CT image.

5. The CT apparatus of claim 1, wherein the image processor is further configured to subtract the second sinogram from the first sinogram, to acquire the third sinogram.

6. The CT apparatus of claim 1, wherein the image processor is further configured to:
model the second portion of the object that is not included in the FOV; and
acquire the third sinogram, using the second portion that is modeled.

7. The CT apparatus of claim 1, wherein the image processor is further configured to iteratively perform a process of updating the first CT image, using the second CT image, and correcting an error in the first CT image, using the first CT image that is updated.

8. The CT apparatus of claim 1, further comprising a display configured to display the second CT image that is obtained by correcting an error in the first CT image.

9. A computed tomography (CT) apparatus comprising:
an image processor configured to:
perform back-protection on a first sinogram that is acquired by a CT scan of an object, to reconstruct a first CT image corresponding to a field of view (FOV);
extract, from the first CT image, a metal component corresponding to a metal that is inserted into the object;
acquire a metal sinogram representing the metal component;
remove the metal component from the first sinogram, using the metal sinogram, to produce a first corrected sinogram;
perform back-projection on the first corrected sinogram to reconstruct a first corrected CT image;
perform forward projection on the first corrected CT image, to acquire a second sinogram representing a first portion of the object that is included in the FOV;
sum the second sinogram and a third sinogram representing a second portion of the object that is not included in the FOV, to acquire a fourth sinogram;
correct the first CT image, based on a difference between the fourth sinogram and the first sinogram, to acquire a second CT image; and
add, to the second CT image, the metal component that is extracted, to produce a second corrected CT image.

10. A CT image reconstructing method comprising:
performing back-projection on a first sinogram that is acquired by a CT scan of an object, to reconstruct a first CT image corresponding to a field of view (FOV);
perform forward projection on the first CT image, to acquire a second sinogram representing a first portion of the object that is included in the FOV;
summing the second sinogram and a third sinogram representing a second portion of the object that is not included in the FOV, to acquire a fourth sinogram; and
correcting the first CT image, based on a difference between the fourth sinogram and the first sinogram, to acquire a second CT image.

11. A CT image reconstructing method comprising:
performing back-projection on a first sinogram that is acquired by a CT scan of an object, to reconstruct a first CT image corresponding to a field of view (FOV);
extracting, from the first CT image, a metal component corresponding to a metal that is inserted into the object;
acquiring a metal sinogram representing the metal component;
removing the metal component from the first sinogram, using the metal sinogram, to produce a first corrected sinogram;
performing back-projection on the first corrected sinogram to reconstruct a first corrected CT image;
performing forward projection on the first corrected CT image, to acquire a second sinogram representing a first portion of the object that is included in the FOV;
summing the second sinogram and a third sinogram representing a second portion of the object that is not included in the FOV, to acquire a fourth sinogram;
correcting the first CT image, based on a difference between the fourth sinogram and the first sinogram, to acquire a second CT image; and
adding, to the second CT image, the metal component that is extracted to product a second corrected CT image.

* * * * *